United States Patent [19]

Kluger et al.

[11] Patent Number: 4,738,985

[45] Date of Patent: Apr. 19, 1988

[54] PHARMACEUTICAL COMPOSITION AND TREATMENT

[75] Inventors: Ronald Kluger, Don Mills; Mortimer Mamelak, Willowdale, both of Canada

[73] Assignee: The University of Toronto Innovations Foundations, Toronto, Canada

[21] Appl. No.: 841,214

[22] Filed: Mar. 19, 1986

Related U.S. Application Data

[63] Continuation-in-part of Ser. No. 637,882, Aug. 6, 1984, Pat. No. 4,599,355.

[51] Int. Cl.$^4$ ............................................. A61K 31/235
[52] U.S. Cl. ...................................................... 514/533
[58] Field of Search ......................................... 514/533

[56] References Cited

PUBLICATIONS

Chem. Abst. 93-148042f (1980).

*Primary Examiner*—Stanley J. Friedman
*Attorney, Agent, or Firm*—Lyon & Lyon

[57] ABSTRACT

Sleep disorders in mammals, such as insomnia and narcolepsy, are treated by administering an effective amount of ethyl 4-acetoxybutanoate, or a closely related homolog thereof. The compounds may also be administered to mammals to cause muscle relaxation and as animal anaesthetics. Moreover the compounds appear to inhibit the release of dopamine in the brain, and are hence useful also in treatment of conditions which are associated with abnormalities of dopamine release and dopamine sensitivities, such as Parkinson's disease, schizophrenia and tardive dyskenesia.

10 Claims, No Drawings

PHARMACEUTICAL COMPOSITION AND TREATMENT

CROSS REFERENCE TO RELATED APPLICATION

This is a Continuation-in-Part of application serial number 06/637,882 filed Aug. 6, 1984 and now U.S. Pat. No. 4,599,355.

FIELD OF THE INVENTION

This invention relates to chemotherapeutic compounds and compositions, useful in the treatment of sleep disorders and other abnormalities in mammals.

BACKGROUND OF THE INVENTION

Sleep disorders are a problem in a large portion of the population. Narcolepsy and insomnia are widely occurring. Safe, non-addictive and long-lasting drugs that are effective are substantially unavailable. Each class of drug currently used for this purpose has major drawbacks. For example, barbiturates have addictive tendencies, act as depressants on the central nervous system, and can be lethal in improper dosages. Benzodiazepines are less effective, and tend to lose their sedative effect with continued use.

BRIEF REFERENCE TO THE PRIOR ART

Hydroxybutyrate is effective in treatment of narcolepsy, and is a very powerful muscle relaxant, but is of only short duration of action, e.g. 2-3 hours. This is a major drawback, since the patient needs to be continually re-awakened for further dosages.

French Medicament Patent No. M.7593 Nordmann et al. discloses the compound ethyl 4-acetoxybutanoate and reports analgesic properties for it. There is no suggestion in this patent of other, unrelated pharmacological properties such as hypnotic or muscle-relaxant properties of compositions containing this compound. The same compound has been detected as a trace component in red wine, as a probable aroma-conferring compound (see Scnreier, "Wine Aroma Composition: Identification of Additional Volatile Constituents of Red Wine", J. Agric. Food Chem., 1980, 28, 926–928).

Laborit et al "Pharmacological Study of Ethyl X-Hydroxybutyrate Glycolate," Agressologie 1974, 15 pp 31–37 attempted to prepare their subject compound, of formula

by reaction of glycolic acid and ethyl γ-bromobutyrate to obtain a compound which might possess the muscle relaxant and antitremorine properties of glycolic acid combined with the hypnotic and cerebral dopamine enhancing properties of sodium gamma-hydroxybutyrate (GHB). There is no proper indication in that publication that Laborit et al actually produced their object compound. Attempts to repeat their described synthesis have been unsuccessful.

SUMMARY OF THE INVENTION

The present invention provides processes, compounds and compositions for use in treatment of sleep disorders such as narcolepsy and insomnia, and for effecting muscle relaxation, in mammals, animal and human. They act as anaesthetics in animals, especially in small animals. The compounds and compositions are also useful in treatment of Parkinson's Disease, schizophrenia and other dopamine related disorders such as tardive dyskenesia in mammals. In treatment of sleep disorders, the compounds have sufficiently long duration of action to overcome the serious disadvantage associated with γ-hydroxybutyrate (GHB). The chemical compounds correspond to the general formula:

where X is a propylene group (-CH$_2$.CH$_2$.CH$_2$—) or an allylene group (—CH=CH—CH$_2$—), optionally substituted with a fluorine group or a C$_1$-C$_6$ lower alkyl group, R is selected from lower alkyl groups having 1–6 carbon atoms, aryl and aralkyl groups of 7–12 carbon atoms, and R$^1$ is selected from lower alkyl groups having 1–6 carbon atoms and benzyl.

DESCRIPTION OF THE PREFERRED EMBODIMENTS

Preferred among the active compound ingredients used in the present invention are those of the above general formula in which X represents an unsubstituted C$_3$ methylene chain i.e. propylene, R is a C$_1$-C$_4$ lower alkyl or phenyl, and R$^1$ is C$_1$-C$_4$ lower alkyl.

Typical and preferred among the compounds used in the present invention is ethyl 4-acetoxybutanoate (also referred to as ethyl 4-0-acetyl 4-hydroxy-butanoate) of formula:

Accordingly, the invention will be further described with reference to that specific compound.

From one aspect ethyl 4-acetoxybutanoate may be regarded as a chemically modified and chemically protected form of γ-hydroxybutyrate (GHB), with the acid and hydroxyl functions thereof protected. GHB has been demonstrated in clinical trials to be a safe, oral drug for treatment of narcolepsy and as a powerful muscle relaxant. However, its effects are of too short a duration, due to its lack of bio-availability. It is possible that, after entry into the cell, the compound ethyl 4-acetoxybutanoate of the invention slowly hydrolyses to form GHB or a similar compound in situ, to exercise the therapeutic effects thereof over a longer period of time. In any event, it has been found that ethyl 4-acetoxybutanoate has a much longer lasting effect, at equivalent dosage levels, than GHB. This makes it a far more effective treatment for narcolepsy than anything heretofore available. Indeed, the effect is so markedly longer lasting that ethyl 4-acetoxybutanoate shows potential for treatment of patients having conditions or disorders where GHB is of little or no use. In cases of chronic insomnia, for example, sufficient dosages of the present compound can be administered to maintain sleep throughout the night, without incurring the development of tolerance or withdrawal side effects. Currently available chemotherapeutic agents will not do this. The compound of the present invention constitutes a safe and powerful hypnotic, for administration to a patient each night. Animals, especially small animals, treated with reasonable doses of ethyl 4-acetoxyoutanoate sleep so deeply that they repose for extended periods of time on their backs. Thus ethyl 4-acetoxybutanoate is useful as a veterinary anaesthetic, especially for small animals. Upon waking, no ill effects are detectable. The compound is also a powerful muscle relaxant for use in the treatment of a variety of conditions involving muscle spasticity.

In addition, ethyl 4-acetoxybutanoate appears to inhibit the release of dopamine in the brain, indicating that it is potentially useful in the treatment of conditions which are associated with abnormalities of dopamine release and dopamine sensitivity, such as schizophrenia and tardive dyskenesia. Another dopamine related disease for which the compounds of the present invention may be used in treatment is Parkinson's disease, although the basis for its use therein is somewhat different. Parkinson's disease is understood to be caused at least in part by degeneration of the dopamine-producing and releasing cells, and is traditionally treated by administration of dopamine to the patient. Administration of ethyl 4-hydroxybutanoate, on the other hand, prior to a night's sleep, temporarily inhibits the release of dopamine from the dopamine-generating cells during the hours of sleep. Consequently, dopamine is stored in the cells during sleep, and released when the effects of ethyl 4-hydroxybutanoate have worn off, i.e. during the waking hours when control of Parkinson's disease is most needed.

A large dose can have an extremely long duration of action (up to 12 hours) without toxic consequences. The duration of action can be controlled by the size of the dosage.

The drug ethyl 4-acetoxybutanoate according to the present invention may be compounded and administered in dosage levels similar to those commonly used for GHB (sodium oxybate, sold under the trade names "Anetamine" and "Somsanit"). Thus it may be orally administered as capsules, in admixture with the usual flavorants, excipients, carriers or the like, such as starch, sugar etc. It may be contained as the pure substance in regular gelatin or soft gelatin capsules, for oral administration, i.e. with gelatin constituting the carrier, or suspended in a non-reactive medium in a capsule. It may be taken orally as a solution or emulsion. It may be injected intraperitoneally or parenterally as a sterile buffered solution or emulsion e.g. in water or physiological saline. Amounts of the order of 5-100 mg per kilogram animal body weight, per nightly dosage, appear suitable in humans, with larger doses (up to three times as much) in animal use. A single dosage unit for once-nightly administration is suitably in the range 0.1-10 g in adult humans, preferably 0.25-5 g, and most preferably 250-1000 mg.

In tests conducted in animal models, the compound ethyl 4-acetoxybutanoate has evidenced extremely low levels of toxicity. In tests conducted with laboratory rats as reported below, doses as high as 3000 mg per kilogram body weight are required, before a toxic level is reached.

Methods of synthesis of compounds used in the present invention are known from the prior art. They may be synthesized, for example, from the appropriate lactone, by reaction thereof with the appropriate alcohol, under acid conditions, to form the hydroxy compound, which is then reacted with an acid anhydride in pyridine. Thus, for the preparation of ethyl 4-acetoxybutanoate, butyrolactone is reacted with ethanol suitably in the presence of sulphuric acid, followed by reaction with acetic anhydride in pyridine. Similar procedures employing methanol instead of ethanol yield the methyl ester. An alternative synthesis involves the reaction of the appropriate carboxylic acid salt with a 4-halo-ester. Thus, by this procedure, ethyl 4-acetoxybutanoate may be prepared by reaction of ethyl 4-chlorobutanoate with potassium acetate in acetic anhydride or acetic acid, following the general procedure of Mereschkowsky (Annalen 431, 231 (1923) and the report by Guest (J.Am. Chem. Soc., 69, 300-302 (1947).

The invention is further described and illustrated in the following specific examples.

EXAMPLE 1—Preparation of Ethyl 4-acetoxybutanoate (also named 4-0-acetyl-4-hydroxybutanoate)

This is a modification of the methods of Spencer and Wright (J.Am. Chem. Soc., 63, 128 (1941) and Meerwein, Borner, Fuchs, Sasse, Schrodt and Spille (Berichte, 89, 2060 (1956).

Eighty grams of butyrolactone was dissolved in 500 ml absolute ethanol containing 8 gms 99% sulfuric acid in a one litre erlenmeyer flask. After 5 days, with powdered sodium carbonate (added carefully until further additions did not produce foaming). Then 20 g anhydrous sodium sulfate was added to dry the solution. The solution was filtered and the filtrate was concentrated on a rotary evaporator in a two litre round bottom flask. The concentrated residue was taken up in 300 ml water and was extracted with three 200 ml portions of chloroform. The chloroform extracts were combined and dried over magnesium sulfate, the solution decanted then concentrated by rotary evaporation. The concentrate was placed in a 1 litre flask clamped in an ice bath, and 80 g acetic anhydride and 100 ml pyridine were added. After addition was complete, the stoppered flask was left overnight with the ice allowed to melt. A solution of 100 ml concentrated hydrochloric acid (12M), 100 ml water and 200 g of ice was prepared and carefully added. Two layers formed, and 100 ml chloroform was added. The aqueous layer was extracted with three 100 ml portions of chloroform. The nonaqueous layer was taken up in chloroform and combined with the extracts. The extract was treated carefully with saturated aqueous sodium bicarbonate in a separatory funnel, followed by shaking, and the aqueous layer was removed. The chloroform layer was then extracted with saturated sodium chloride solution then dried over anhydrous magnesium sulfate, and filtered. The dried solution was concentrated on a rotary evaporator, then distilled at 0.1 torr on a 1 cm by 10 cm vacuum jacketed column. The product is collected at 56° C, and shown by nmr spectroscopy to be pure ethyl 4-acetoxybutanoate Yield: 35 g.

By repeating the above procedure, but substituting methanol for ethanol, methyl 4-acetoxybutanoate was similarly prepared.

EXAMPLE 2—Preparation of methyl 4-acetoxybutanoate

To a 500 ml round bottom flask, equipped with teflax apparatus, 14.7 g (0.15 ml) of potassium acetate was dissolved in 185 ml acetic anhydride. 1.87 g potassium iodide (0.0113 mol) was subsequently dissolved into this heterogeneous mixture. After addition of 18.3 ml (0.15 mol) of methyl 4-chlorobutanoate, the mixture was refluxed gently for 24 hours. Upon completion of reflux, the apparatus was allowed to cool slowly to room temperature and the precipitate was removed via suction filtration (15 Torr) and washed with ethyl acetate. After rotary evaporation (15 Torr), distillation under vacuum (1.5 Torr) of the orange solution yielded three fractions:

(1) Acetic anhydride, 35°-40° C.;
(2) Acetic anhydride+product, 41°-80° C.
(3) Product 81°-92° C. (levelled off at 92° C.).

Fraction 2 was redistilled and combined with (3) to give 22.96g of methyl 4-acetoxybutanoate (96% of theoretical).

EXAMPLE 3—Preparation of Methyl 4-benzoyloxbutanoate 21.6 g (0.15 mol) of sodium benzoate was added slowly with stirring to 240 dimethyl formamide in a 500 ml round bottom flask. Upon addition of 1.87 g (0.0113 mol) potassium iodide followed by 18.3 ml (0.15 mol) of methyl 4-chlorobutanoate the mixture was refluxed gently for 24 hours. After reflux the reaction vessel was allowed to cool slowly to room temperature and the precipitate was removed via suction filtration (15 Torr) and washed with ethyl acetate. After rotary evaporation (15 Torr) to remove ethyl acetate distillation under vacuum yielded three distinct fractions:

(1) DMF at 35° C.
(2) DMF at 65°-72° C.
(3) Product 110°-150° C. (levelled off at 148° C.).

During the collection of the product, the condenser had to be turned off in order to avoid crystallization of the product. The yield of methyl 4-benzoyloxybutanoate was 26.86 g (80.6% of theoretical yield).

EXAMPLE 4

The preferred compound according to the invention was administered to laboratory rats, and the sleep of the animals induced by the drug was tracked by means of an electroencephalograph.

Compound ethyl 4-acetoxybutanoate, administered by mouth at a dosage of 250 mg per kilogram body weight induced sleep for 1 hour 28 minutes. At a dosage of 500 mg per kilogram administered in one case by mouth and in another case intraperitoneally, sleep was induced for 4 hours. In all cases, the limbs and other body joints were quite flaccid, indicating a high degree of muscle relaxation. Upon waking, none of the animals exhibited ill effects.

The administration to a similar laboratory rat, intraperitoneally, of a dosage of 500 mg per kilogram body weight of GHB induced sleep for only 1 hour 59 minutes, by contrast.

EXAMPLE 5

The effects on sleep and righting time of the oral and intraperitoneal administration of the prior art compound hydroxybutyrate sodium salt (GHB) and 4-acetoxybutanoate (EAB) according to the invention were determined, using groups of laboratory rats.

In a first experiment, GHB was administered at high dosage level (25 mM/kg or 3gm/kg body weight) orally to three animals. None of the animals slept, confirming literature reports that GHB is ineffective in high doses administered orally. The most likely reason is that oral GHB is poorly absorbed.

In a second experiment each of GHB and EAB was given to separate groups of twelve and eleven animals respectively, by oral administration at the same, lower dosage level of 10mM/kg body weight. The results are given in Table 1 below, in which an asterisk indicates that the animal could be placed on its back for the time indicated, AVG 1 is the average time of sleep based only on the animals of the group which slept, and AVG 2 is the average sleep time of all the rats, whether they slept or not. DNS signifies "did not sleep".

TABLE 1

| Drug | | | |
|---|---|---|---|
| GHB | | EAB | |
| ANIMAL # | TIME SLEPT (mins) | ANIMAL # | TIME SLEPT (mins) |
| 1 | 64.70 | 13 | 120.30 |
| 2 | DNS | 14 | 106.10 |
| 3 | DNS | 15 | 125.75 |
| 4 | 60.80 | 16 | 143.45 |
| 5 | 55.80 | 17 | 300.20* |
| 6 | DNS | 18 | 120.00 |
| 7 | 74.70 | 19 | 175.80 |
| 8 | 72.80 | 20 | 331.60* |
| 9 | DNS | 21 | 311.50* |
| 10 | DNS | 22 | 317.65* |
| 11 | DNS | 23 | 103.90 |
| 12 | DNS | | |
| RANGE | 0–74.7 | RANGE | 103.9–331.6 |
| AVG 1 | 65.76 | AVG 1 | 170.57 |
| AVG 2 | 27.40 | | |

These results indicate that a high dose of oral GHB has weak effects. Only five out of twelve animals were put to sleep, and none of them could be placed on their backs. A comparable dose of EAB put all rats to sleep, and four of eleven could be placed on their backs for more than five hours, indicating a deep level of sleep, and effectiveness of the dosage as an animal anaestnetic. This experiment indicates that EAB is effective when given by mouth, and that it is long acting. Moreover, it was observed that the limbs and joints of the animals to which EAB had been administered were, during sleep, loose and flaccid, indicating a high degree of muscle relaxation. No sign of toxicity was observed in the animals treated with EAB, showing that, if the compound shows any toxicity at all, it is at a level well above the effective dosage levels. Upon waking, none of the animals exhibited any ill effects.

EXAMPLE 6

Equivalent doses (5 mM/kg body weight) of GHB and EAB were administered intraperitoneally to two separate groups of rats, six animals per group, and the effects on sleep and righting time determined. The results are given in Table 2 below, which bears the same legends as Table 1.

TABLE 2

| Drug | | | |
|---|---|---|---|
| GHB | | EAB | |
| ANIMAL # | TIME SLEPT (mins) | ANIMAL # | TIME SLEPT (mins) |
| 1 | DNS | 7 | 51.70* |
| 2 | 70.20* | 8 | 39.30* |
| 3 | DNS | 9 | 199.65* |
| 4 | 55.40* | 10 | 141.70* |
| 5 | 75.20* | 11 | 70.00* |
| 6 | 87.35* | 12 | 259.00* |
| RANGE | 0–87.35 | RANGE | 39.30–259.00 |
| AVG 1 | 72.04 | AVG 1 | 126.89 |
| AVG 2 | 48.03 | | |

These data indicate that the effects of EAB are more powerful and longer lasting, even when given intraperitoneally. Thus, the elimination of EAB from the body's system is slower than that of GHB. Again, the animals sleeping under the influence of EAB exhibited a high degree of muscle relaxation. Upon walking, none of them showed any ill effects.

We claim:

1. A process of causing muscle relaxation in a mammal or treating a dopamine-related abnormality in a mammal, which comprises administering to the mammal an effective amount of a pharmaceutical composition containing as active ingredient a compound of general formula:

$$R.CO.O.X.CO.OR^1$$

in which X is a propylene group or an allylene group optionally substituted with a fluorine group or a $C_1-C_6$ lower alkyl group, R is selected from lower alkyl groups having 1-6 carbon atoms, aryl groups and aralkyl groups having 7-12 carbon atoms, and $R^1$ is selected from lower alkyl groups having 1-6 carbon atoms and benzyl.

2. The process of claim 1 where X represents an unsubstituted $C_3$ methylene chain, R is a $C_1-C_4$ lower alkyl or phenyl and $R^1$ is a $C_1-C_4$ lower alkyl.

3. The process of claim 2 wherein the pharmaceutical composition is administered to a dopamine related abnormality suffering mammal.

4. The process of claim 3 wherein the active ingredient in the composition is selected from ethyl 4-acetoxybutanoate; methyl 4-acetoxybutanoate; and methyl 4-benzoylbutanoate.

5. The process of claim 4 wherein the active ingredient in the composition is ethyl 4-acetoxybutanoate.

6. The process of claim 5 wherein the composition is administered at a dosage of from about 5 mg to about 100 mg of active ingredient per kilogram mammal body weight.

7. The process of claim 2 wherein the pharmaceutical composition is adminstered to effect muscle relaxation in the patient mammal.

8. The process of claim 2 wherein the compound is selected from ethyl 4-acetoxybutanoate; methyl 4-acetoxybutanoate; and methyl 4-benzoylbutanoate.

9. The process of claim 8 wherein the compound is ethyl 4-acetoxybutanoate.

10. The process of claim 9 wherein the composition is administered at a dosage of from about 5 mg to about 100 mg of active ingredient per kilogram mammal body weight.

* * * * *